US00PP08653P

United States Patent [19]

van Leeuwen

[11] Patent Number: Plant 8,653

[45] Date of Patent: Mar. 22, 1994

[54] CARNATION NAMED REDDYPOT

[75] Inventor: Gijsbertus van Leeuwen, CN S Gravenzande, Netherlands

[73] Assignee: West Stek b.v., Netherlands

[21] Appl. No.: 985,014

[22] Filed: Dec. 3, 1992

[51] Int. Cl.[5] ..... A01H 5/00

[52] U.S. Cl. ..... Plt./70.7

[58] Field of Search ..... Plt. 70.7

*Primary Examiner*—Howard J. Locker

*Assistant Examiner*—Elizabeth C. Kemmerer

*Attorney, Agent, or Firm*—Tilton, Fallon, Lungmus & Chestnut

[57] ABSTRACT

A new and distinctive pot carnation cultivar particularly distinguished by its profuse, continuous production of small flowers borne singly on strong, upright pedicels, with one flower with some smaller buds spaced vertically at the top of a stem, the petals of which are predominantly velvet red with a light green base, the edges of which are slightly serrated.

1 Drawing Sheet

BACKGROUND OF THE NEW PLANT

This carnation cultivar originated as a sport of parent variety "Pinky" produced in my nursery at Kwintsheul, The Netherlands. The claimed plant, hereinafter identified, was selected from a field of various carnation varieties maintained at my nursery for breeding purposes. This particular sport was selected because of the very unusual flower coloration and shape of the petal and its sturdy, and year around growth habit. The new carnation cultivar most closely resembles "Pinky" but the new cultivar has bigger flowers, different colors and grows more quickly. This selected sport was propagated by me at Kwintsheul, The Netherlands, by cuttings with very satisfactory results and thereafter this selected plant was propagated through several successive generations in the same manner which demonstrated conclusively that the novel characteristics of the originally selected sport would be maintained from generation to generation and its homogeneity would be firmly established.

DESCRIPTION OF THE DRAWING

My new carnation plant is illustrated by the accompanying photographic drawing which, in full color, shows the form and coloration of the flowers as they appear with relatively close spacing at the upper end portion of the flowering stem of the plant. The colors shown are as nearly true to these herein specified as is reasonably possible to obtain by conventional photographic procedures.

DESCRIPTION OF THE NEW PLANT

The following is a detailed description of my new carnation plant as observed from plants grown under greenhouse conditions in Kwintsheul, The Netherlands, with the stated flower colors being according to The R.H.S. Colour Chart of The Royal Horticultural Society of London, England.

THE PLANT

Origin: Sport.

Parentage: "Pinky".

The parent plant is so identified in my business records of the present cultivar maintained at the offices of the Kwintsheul, The Netherlands, nursery and the production of the aforementioned sport are also recorded.

Classification:

*Botanic.*—*Dianthus caryophyllus.*

*Commercial.*—Pot Carnation.

Form: A short upright bush.

Height: About 15 cm.

Growth rate: Flowering in about three months following the first planting.

Main stem length: About 11 cm.

Strength: Normal-stem thickness about 3 mm.

Branching character: Very good, about 10 breaks.

Growth: Upright.

Foliage:

*Quantity.*—Abundant.

Number of leaves.—Approximately 16 pairs of leaves per stem.

*Size and shape of leaf.*—The leaves are elliptical shaped and are between 2.5-8 cm in length and have a width of about 6 mm.

*Texture.*—Leathery.

The BUD

Size: Small.

Shape: Ovoid.

Diameter: Approximately 9 mm.

Length: Approximately 17 mm.

Rate of opening: Bud to flower in about 4 days.

Color of petals: When sepals first divide, velvet red. When petals begin to unfurl, velvet red.

Sepals:

*Shape.*—Cylindrical.

*Number.*—Five connected together.

*Color.*—Inside — Olive green with red tips. Outside — Olive green with red tips.

Calyx:

*Shape.*—Pear shaped.

*Aspect.*—Smooth.

*Size.*—Small about 9 mm. wide and 17 mm. long.

*Splitting.*—Slightly for about 8 mm. from the top.

THE FLOWER

Blooming habit: Continuous and profuse — all seasons, (has a tendency to give few blooms in the Fall).

Size of bloom: Small.

*Diameter.*—Approximately 33 mm.

*Depth.*—Approximately 9 mm.

Borne: Singly on strong, upright pedicels, with one flower spaced vertically at the top of a stem.

Shape: High center.

Petalage:

*Number of petals.*—Approximately nineteen.

*Arrangement.*—Imbricated.

*Texture.*—Leathery.

*Form.*—Fan Shaped.

*Margin type.*—Slightly serrated.

*Appearance.*—Satiny.

*Color.*—The color of the body of the petals is RHS 53-A. However, towards the base of the petal the color changes to RHS 60-A/RHS 60-B. The color of the base is light green. The color of the reverse side is RHS 60-B.

Discoloration after full bloom: None.

Persistence: The petals of matured flowers hang on and dry.

Fragrance: Light.

Lasting quality: On the plant, about 7 days.

Flower stem:

*Length.*—About 110 mm.

*Character.*—Upright and sturdy.

*Color.*—Olive-green.

THE REPRODUCTIVE ORGANS

Stamens:

*Number.*—About 8.

*Arrangement.*—Clustered.

*Anthers.*—Size: Approximately 2 mm. Color: Violet.

*Filaments.*—Length: About 8 mm. Color: Light green.

*Pollen.*—Color: Violet.

Pistils:

*Number.*—One.

*Styles.*—Length about 12 mm. and cream colored with violet top.

*Stigmas.*—Cream with violet top.

Ovaries:

*Character of ovaries.*—Superior.

*Color.*—Light green to yellow.

*Fertility.*—The plant is not fertile.

I claim:

1. A new and distinctive pot carnation plant, substantially as herein shown and described, characterized by its profuse, continuous production of small sized light violet flowers with light green base with slightly serrated edge, said flowers being borne singly on strong, upright pedicels, with one flower spaced vertically at the top of the stem.

* * * * *

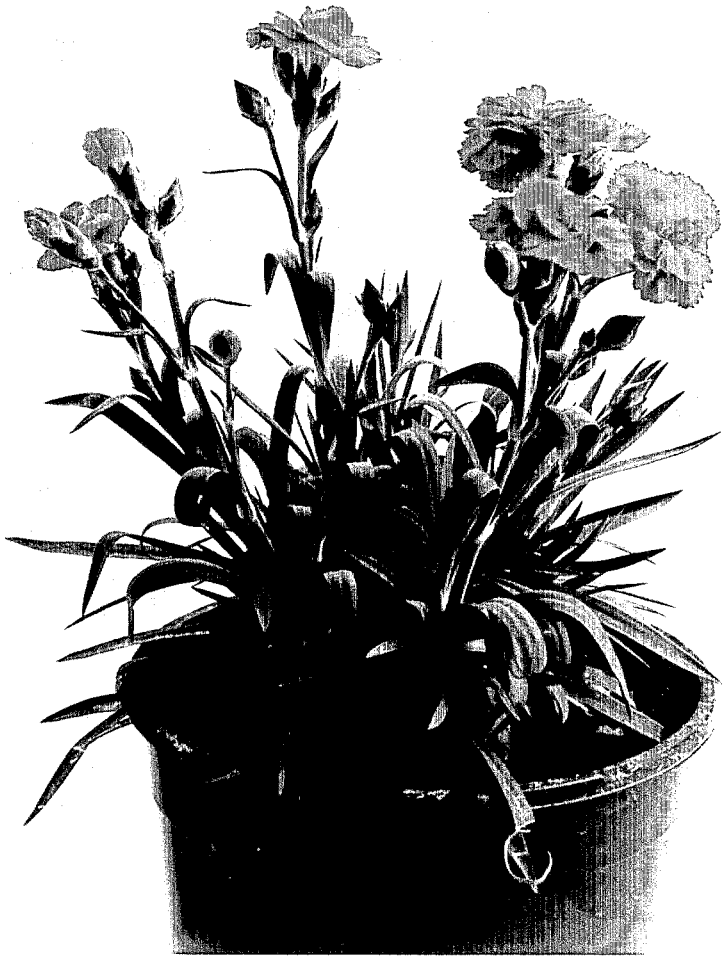

UNITED STATES PATENT AND TRADEMARK OFFICE

CERTIFICATE OF CORRECTION

PATENT NO. : PP 8653

DATED : March 22, 1994

INVENTOR(S) : Van Leeuwen

It is certified that error appears in the above-indentified patent and that said Letters Patent is hereby corrected as shown below:

Column 2, line 21, after "6 mm." insert -- Color: RHS 136A--.

Signed and Sealed this

Twenty-fifth Day of October, 1994

*Attest:*

Bruce Lehman

BRUCE LEHMAN

*Attesting Officer*

*Commissioner of Patents and Trademarks*